United States Patent
Chen et al.

(10) Patent No.: US 12,386,000 B2
(45) Date of Patent: Aug. 12, 2025

(54) METHOD AND APPARATUS FOR QUANTITATIVE MAGNETIC RESONANCE IMAGING USING SPIN-LOCK RADIO FREQUENCY TRAINS

(71) Applicants: ILLUMINATIO MEDICAL TECHNOLOGY LIMITED, Hong Kong (CN); THE CHINESE UNIVERSITY OF HONG KONG (CUHK), Hong Kong (CN)

(72) Inventors: Weitian Chen, Hong Kong (CN); Baiyan Jiang, Hong Kong (CN); Ziqang Yu, Hong Kong (CN)

(73) Assignees: Illuminatio Medical Technology Limited, Hong Kong (CN); The Chinese University of Hong Kong (CUHK), Hong Kong (CN)

( * ) Notice: Subject to any disclaimer, the term of this patent is extended or adjusted under 35 U.S.C. 154(b) by 149 days.

(21) Appl. No.: 18/204,385

(22) Filed: May 31, 2023

(65) Prior Publication Data
US 2024/0402275 A1    Dec. 5, 2024

Related U.S. Application Data

(60) Provisional application No. 63/326,766, filed on Apr. 1, 2022.

(51) Int. Cl.
*G01R 33/50* (2006.01)
*G01R 33/56* (2006.01)

(52) U.S. Cl.
CPC ......... *G01R 33/50* (2013.01); *G01R 33/5608* (2013.01)

(58) Field of Classification Search
CPC .......................... G01R 33/50; G01R 33/5608
See application file for complete search history.

(56) References Cited

U.S. PATENT DOCUMENTS

| | | | |
|---|---|---|---|
| 5,281,917 A | 1/1994 | Santyr | |
| 8,406,849 B2 * | 3/2013 | Jeong | G01R 33/5616 324/309 |

(Continued)

FOREIGN PATENT DOCUMENTS

| | | |
|---|---|---|
| CN | 112748381 A | 5/2021 |
| EP | 2975424 A1 | 1/2016 |
| JP | 2013121437 A | 6/2013 |

OTHER PUBLICATIONS

International Search Report issued in Application No. PCT/IB2023/053377, dated Aug. 21, 2023,(3p).

(Continued)

*Primary Examiner* — Gregory H Curran
(74) *Attorney, Agent, or Firm* — Arch & Lake LLP

(57) ABSTRACT

A method for quantitative magnetic resonance imaging (MRI), an apparatus, and a non-transitory computer-readable storage medium are provided. In the method, a first magnetization signal is obtained based on a first train of spin-lock modules. Additionally, a second magnetization signal is obtained based on a second train of spin-lock modules. A final magnetization is obtained based on the first magnetization signal and the second magnetization signal. These processes are repeated to collect one or more final magnetization signals for quantification of tissue parameters.

20 Claims, 3 Drawing Sheets

(56) References Cited

U.S. PATENT DOCUMENTS

| | | | |
|---|---|---|---|
| 8,618,797 B2 * | 12/2013 | Chen | G01R 33/5602 |
| | | | 324/318 |
| 2006/0043970 A1 | 3/2006 | Zaharchuk et al. | |
| 2013/0300416 A1 * | 11/2013 | Welch | G01R 33/32 |
| | | | 324/309 |
| 2018/0031661 A1 | 2/2018 | Chen et al. | |
| 2018/0143276 A1 | 5/2018 | Wendell et al. | |
| 2021/0141041 A1 | 5/2021 | Chen et al. | |

OTHER PUBLICATIONS

Jian Hou, et al., the Chinese University of Hong Kong, Hong Kong SAR, China, "Macromolecular proton fraction mapping based on spin-lock magnetic resonance imaging", Magnetic resonance in Medicine, DOI: 10.1002/mrm.28362 (15p).

* cited by examiner

METHOD AND APPARATUS FOR QUANTITATIVE MAGNETIC RESONANCE IMAGING USING SPIN-LOCK RADIO FREQUENCY TRAINS

CROSS-REFERENCE TO RELATED APPLICATION

This application is based upon and claims priority to Provisional Application No. 63/326,766, filed on Apr. 1, 2022, the entire content of which is incorporated herein by reference for all purposes.

TECHNICAL FIELD

The present disclosure is related to the field of Magnetic Resonance Imaging (MRI) system imaging, and more particularly, to a method and apparatus for quantitative magnetic resonance imaging using spin-lock radio frequency trains.

BACKGROUND

MRI is among the most widely used non-invasive imaging modalities in clinical diagnosis. In recent years, its ability to probe diseases at a molecular level has elicited increasing interest in both clinical and research settings. There are two types of molecular signal that are widely studied in MRI field, namely Chemical Exchange (CE) and Magnetization Transfer (MT).

Generally, it is popular of using off-resonance saturation radiofrequency (RF) pulses to study CE and MT based contrasts. Principally, it is based on the exchange or the transfer of saturated biological molecule protons or bond water protons of macromolecules with free water protons, which are saturated by applying a selective off-resonance RF pulse. This effect results in water signal attenuation, which allows indirect measurement of CE and MT signal.

Alternatively, spin-lock-based techniques can also be used to measure CE and MT signal. Spin-lock is achieved by applying a radiofrequency (RF) pulse to the magnetization to align the magnetization along an effective spin-lock field. The resulting MR signal decays with a time constant $T_{1\rho}$ that is related to an amplitude of the effective spin-lock field dependent on the amplitude of spin-lock pulse ($\gamma B_1/2\pi$) and the resonance frequency offset of spin-lock pulse.

Generally, the duration and amplitude of spin-lock RF pulses are crucial parameters for spin-lock-based techniques. They play an important role in assessment of biochemical properties of tissues. However, the maximum duration of the spin-lock RF pulse is limited by the hardware of MRI system and the Specific Absorption Rate (SAR). Employ a train of spin-lock pulse with a short duration of each individual RF pulse can be used to mitigate this problem. However, it is important to note that, unlike a single spin-lock pulse, the relaxation model of using a train of spin-lock RF pulses is highly complicated and a conventional mono-exponential model cannot be used for quantification in this case. This imposes great challenges in quantification when a train of spin-lock RF pulses is used.

SUMMARY

Examples of the present disclosure provide methods and apparatus for quantitative magnetic resonance imaging using spin-lock radio frequency trains.

According to a first aspect of the present disclosure, a method for quantitative magnetic resonance imaging (MRI) is provided. The method includes: obtaining a first magnetization signal based on a first train of spin-lock modules, obtaining a second magnetization based on a second train of spin-lock modules, and obtaining a final magnetization signal based on the first magnetization signal and the second magnetization signal.

According to a second aspect of the present disclosure, an apparatus for quantitative MRI is provided. The apparatus includes one or more processors and a memory configured to store instructions executable by the one or more processors. Further, the one or more processors, upon execution of the instructions, are configured to perform acts including: obtaining a first magnetization signal based on a first train of spin-lock modules, obtaining a second magnetization based on a second train of spin-lock modules, and obtaining a final magnetization signal based on the first magnetization signal and the second magnetization signal.

According to a third aspect of the present disclosure, a non-transitory computer-readable storage medium is provided. The medium stores computer-executable instructions that, when executed by one or more computer processors, cause the one or more computer processors to perform acts including: obtaining a first magnetization signal based on a first train of spin-lock modules, obtaining a second magnetization based on a second train of spin-lock modules, and obtaining a final magnetization signal based on the first magnetization signal and the second magnetization signal.

One or more final magnetizations are obtained by repeating the aforementioned processes and are used for quantification of ore or more tissue parameters.

It is to be understood that the above general descriptions and detailed descriptions below are only exemplary and explanatory and not intended to limit the present disclosure.

BRIEF DESCRIPTION OF THE DRAWINGS

The accompanying drawings, which are incorporated in and constitute a part of this specification, illustrate examples consistent with the present disclosure and, together with the description, serve to explain the principles of the disclosure.

DETAILED DESCRIPTION

Figure 1:
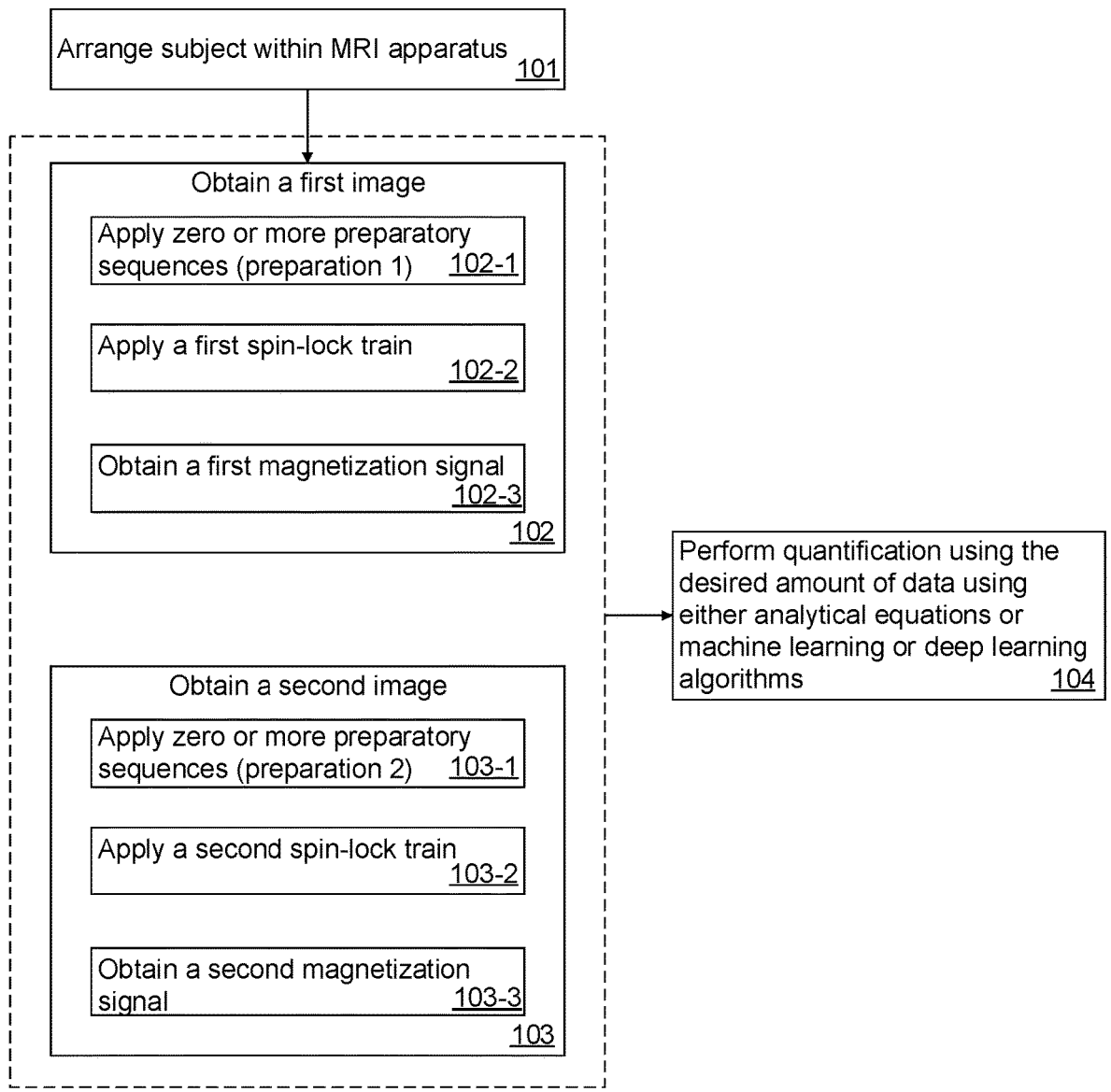
FIG. 1 is a flow chart illustrating a method for quantitative magnetic resonance imaging using spin-lock radio frequency trains in accordance with some examples of the present disclosure.

Reference will now be made in detail to example embodiments, examples of which are illustrated in the accompanying drawings. The following description refers to the accompanying drawings in which the same numbers in different drawings represent the same or similar elements unless otherwise represented. The implementations set forth in the following description of example embodiments do not represent all implementations consistent with the disclosure. Instead, they are merely examples of apparatuses and methods consistent with aspects related to the disclosure as recited in the appended claims.

The terminology used in the present disclosure is for the purpose of describing particular embodiments only and is not intended to limit the present disclosure. As used in the present disclosure and the appended claims, the singular forms "a," "an," and "the" are intended to include the plural forms as well, unless the context clearly indicates otherwise. It shall also be understood that the term "and/or" used herein is intended to signify and include any or all possible combinations of one or more of the associated listed items.

It shall be understood that, although the terms "first," "second," "third," etc., may be used herein to describe various information, the information should not be limited by these terms. These terms are only used to distinguish one category of information from another. For example, without departing from the scope of the present disclosure, first information may be termed as second information; and similarly, second information may also be termed as first information. As used herein, the term "if" may be understood to mean "when" or "upon" or "in response to a judgment" depending on the context.

Reference throughout this specification to "one embodiment," "an embodiment," "an example," "some embodiments," "some examples," or similar language means that a particular feature, structure, or characteristic described is included in at least one embodiment or example. Features, structures, elements, or characteristics described in connection with one or some embodiments are also applicable to other embodiments, unless expressly specified otherwise.

For making it convenient for those skilled in the art to understand, multiple implementation modes are listed in the embodiments of the disclosure to describe the technical solutions of the embodiments of the disclosure clearly. Of course, those skilled in the art can understood that multiple embodiments provided in the embodiments of the disclosure can be executed independently, or can be combined with methods of the other embodiments in the embodiments of the disclosure for execution together, or may be executed independently or after combined with some methods in other related technologies. No limits are made thereto in the embodiments of the disclosure.

The present disclosure provides methods and apparatuses for simplifying the quantification of $T_{1\rho}$ using spin-lock radiofrequency trains. Additionally, the present disclosure provides methods and devices to quantify tissue parameters related to magnetization transfer using spin-lock radiofrequency trains based on off-resonance spin-lock. Spin-lock radiofrequency (RF) trains are a type of MRI pulse sequence that is used to manipulate the magnetization of protons in the body. Spin-lock RF trains may be composed of a series of spin-lock modules that are applied at a specified frequency and duration.

In some examples according to the present disclosure, a pulse sequence of trains of spin-lock modules may contain multiple spin-lock modules. In a spin-lock RF train, a spin-lock module may include a set of RF pulses that are applied to the tissue in a specific pattern to create a spin-lock field. Spin-lock is a specialized MRI technique used to manipulate spins by using RF pulses. This technique is particularly useful for investigating various molecular-scale interactions, measuring relaxation rates, and studying tissue properties.

For example, a spin-lock module may consist of a spin-lock RF cluster followed by an idle time without RF irradiation with a duration of Td. The spin-lock RF cluster includes a spin-lock RF pulse with duration time-of-spin-lock (TSL) sandwiched by a head RF pulse and a tail RF pulse, where the head RF pulse may be a RF pulse before the spin-lock RF pulse and the tail RF pulse may be a RF pulse after the spin-lock RF pulse. Crusher gradients may be added after each spin-lock RF cluster to de-phase transverse magnetizations. The parameters of each spin-lock module, including but not limited to TSL, Td, phase of RF pulses, the orientation of spin-lock field, and the area of crusher can vary for different spin-lock modules.

Figure 3:
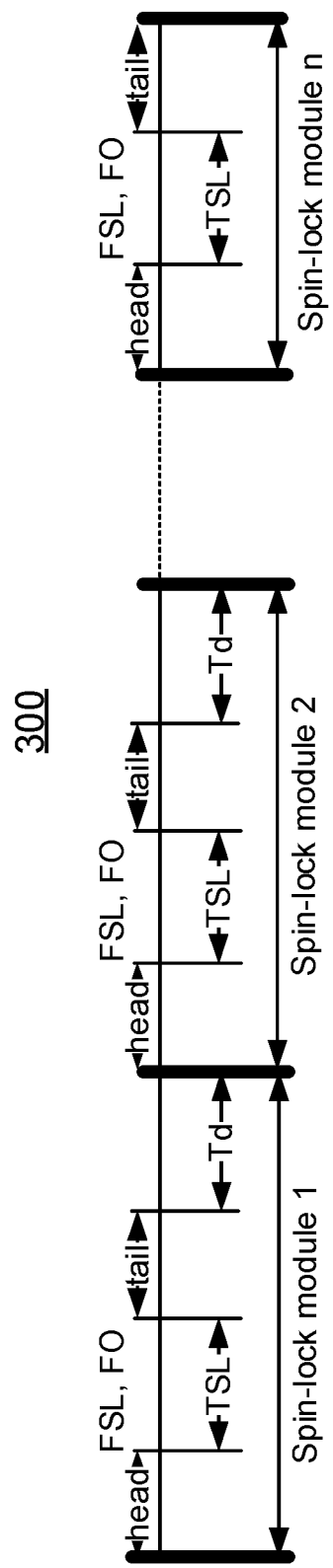
FIG. 3 a pulse sequence including multiple repeating spin-lock modules in accordance with some examples according to the present disclosure.

FIG. 3 illustrates a pulse sequence including multiple spin-lock modules in accordance with some examples according to the present disclosure. As shown in FIG. 3, the pulse sequence 300 includes a plurality of spin-lock modules 1-$n$, where n is the number of spin-lock modules. At least one spin-lock module except the last spin-lock module n includes a spin lock RF cluster followed by an idle time without RF irradiation with a duration of Td. The spin lock RF cluster includes the spin-lock RF pulse with a duration of the TSL, the head RF pulse, and the tail RF pulse, where the spin-lock RF pulse is sandwiched between the head and the tail RF pulse. As shown in FIG. 3, the amplitude of the spin lock RF pulse is represented by Frequency of Spin-lock (FSL), and the resonance frequency offset of the spin-lock RF pulse is represented by frequency offset (FO). The last spin-lock module, the spin-lock module n as shown in FIG. 3, includes the head RF pulse, the spin-lock RF pulse with the duration of the TSL, and the tail RF pulse, where the spin-lock RF pulse is sandwiched between the head and the tail RF pulse.

For a spin-lock module with a spin-lock RF pulse with the duration TSL and a constant RF amplitude, the magnetization M at the end of a spin-lock module can be expressed by following equation (1):

$$M = M_{ini}e^{-R_{1\rho}TSL} + M_{ss}(1 - e^{-R_{1\rho}TSL}), \qquad (1)$$

where $M_{ini}$ is the initial magnetization after the head RF pulse and before the spin-lock RF pulse in the first spin-lock module in a spin-lock radiofrequency train; $R_{1\rho(=1/T_1\rho)}$ is the spin-lattice relaxation rate in the rotating frame; $M_{ss}$ is the steady state magnetization. A train with multiple spin-lock modules can achieve a much longer total TSL compared to a single spin-lock module. In the presence of a train of 2 or more spin-lock modules, the magnetization at the end of the train of spin-lock modules denoted as $M_{sl\_train\_1}$ can be derived using the equation (2) and T1 relaxation during the idle time Td:

$$M_{sl\_train\_1} = (M_{ini} - M_{ss})e^{-R_{1\rho}TSL \cdot n}e^{-R_1 Td \cdot (n-1)} + \qquad (2)$$
$$(M_{ss} - M_0)\left[\left(e^{-R_1 Td} \cdot e^{-R_{1\rho}TSL} - e^{-R_{1\rho}TSL}\right) \cdot a_{n-1}\right] + M_{ss},$$

where $R_1(=1/T1)$ is the tissue spin-lattice relaxation rate; n is the number of spin-lock modules in the spin-lock train; and $M_0$ is the equilibrium magnetization. The $a_{n-1}$ is a recursive formula and is defined as $$\begin{cases} a_1 = 1, \\ a_n = e^{-R_1 Td} \cdot e^{-R_{1\rho}TSL} \cdot a_{n-1} + 1, \end{cases}$$

for n≥2.

In some examples of the present disclosure, a second magnetization signal is acquired with different initial magnetization $M_{ini2}$ but the same stead-state magnetization $M_{ss}$.

The magnetization at the end of spin-lock train in second acquisition as $M_{sl\_train\_2}$ may be obtained based on the equation (3) as follows:

$$M_{sl\_train\_2} = (M_{ini2} - M_{ss})e^{-R_{1\rho}TSL \cdot n}e^{-R_1 Td \cdot (n-1)} + \quad (3)$$
$$(M_{ss} - M_0)\left[\left(e^{-R_1 Td} \cdot e^{-R_{1\rho}TSL} - e^{-R_{1\rho}TSL}\right) \cdot a_{n-1}\right] + M_{ss},$$

$M_{ini}$ may be modified by, but not limited to, following approaches. In some examples, the spin-lock radio frequency trains are performed after different time durations of relaxation (T1 and/or T2). Thus, different degree of magnetization relaxation can result in different $M_{ini}$.

In some other examples, the attributes of the head RF pulse of the first spin-lock module in the train are manipulated to alter $M_{ini}$. The attributes may include the phase, the frequency modulation, duration, amplitude, etc.

In some other examples, one or more RF pulses may be used in front of the spin-lock radiofrequency trains to alter $M_{ini}$. This RF pulse can have arbitrary flip angle, phase, frequency modulation, duration, amplitude, etc. Spoiling gradient may be applied after each of these RF pulses.

By subtracting the equation (2) from the equation (3) or vice versa, the magnetization equation may be essentially simplified into a simple mono-exponential model that allows convenient quantification of $R_{1\rho}$ (=1/$T_{1\rho}$):

$$M_{fin} = M_{sl\_train\_2} - M_{sl\_train} = (M_{ini2} - M_{ini})e^{-R_{1\rho}TSL \cdot n}e^{-R_1 Td \cdot (n-1)}. \quad (4)$$

In some examples, the term $(M_{ini2}-M_{ini})e^{-R_1 Td \cdot (n-1)}$ is independent of TSL. Thus, by collecting $M_{fin}$ with different TSL, $M_{fin}$ may be fit to a mono-exponential model to obtain $R_{1\rho}$.

In some examples, the spin-lock RF pulse clusters may be applied either on-resonance or off-resonance. For on-resonance, the spin-lock RF pulse is tuned to on-resonance Larmor frequency, and the magnetization is spin-locked in the transverse plane. For off-resonance spin-lock, the spin-lock RF pulse is tuned to at a resonance frequency offset $\Delta\omega$ from the on-resonance Larmor frequency, and the magnetization is spin-locked at an angle from the transverse plane, which is determined by $\Delta\omega$ and the spin-lock RF amplitude $\omega_1$. The present disclosure may be used for quantification of $R_{1\rho}$ both at on-resonance and off-resonance spin-lock.

According to the present disclosure, using trains of spin-lock RF pulses for quantitative MRI may also be used to quantify tissue parameters related to magnetization transfer by employing a train of off-resonance spin-lock RF modules. By using a train of off-resonance spin-lock modules and follow the aforementioned steps to acquire data at different $M_{ini}$, $M_{fin}$ may be obtained as shown in equation (4).

In some examples, by adjusting MRI pulse sequence parameters of trains of spin-lock RF pulse, the acquired signal will be more sensitive to specific tissue parameter related to magnetization transfer, such as macromolecule proton fraction (MPF, also known as bound pool fraction (BPF), or other terms), compared to the other tissue parameters related to magnetization transfer.

In some examples, the pulse sequence parameters of each individual spin-lock module in a train of spin-lock modules may vary when collecting magnetization signal. These pulse sequence parameters include but not limited to TSL, Td, area of crusher gradient, orientation of spin-lock field etc.

Machine learning or deep learning can be used to quantify data acquired using trains of spin-lock RF pulse with varying parameters.

In some examples, datasets may be collected at various $\Delta\omega$ and $\omega_1$ as follows. Here $\Delta\omega$ is the resonance frequency offset of spin-lock, and $\omega_1$ is the amplitude of spin-lock RF pulse. For example, a first image of $M_{fin}$ as shown in equation (4) is acquired by using a train of spin-lock pulses with characteristics $(\Delta\omega=\Delta\omega^{(1)}, \omega_1=\omega_1^{(1)})$.

Similarly, a second image of $M_{fin}$ as shown equation (4) is acquired in the same manner as the first image of $M_{fin}$ by using a train of spin-lock pulses with characteristics $((\Delta\omega=\Delta\omega^{(2)}, \omega_1=\omega_1^{(2)})$.

Moreover, the third or more image images of $M_{fin}$ as shown in equation (4) may be further acquired. By using the spin-lock pulse trains with $(\Delta\omega=\Delta\omega^{(i)}), \omega_1=\omega_1^{(i)}$), where i=3, 4 . . . . N and N is the total number of images of $M_{fin}$ as shown equation (4).

Under the condition that $$\frac{\Delta\omega}{\omega_1}$$

is unchanged, a parameter $R_{mpfsl}$ can be calculated from a pair of $M_{fin}$ as following:

$$R_{mpfsl} = \frac{abs\left(\log\left(\frac{M_{fin,1}}{M_{fin,2}}\right)\right)}{TSL \cdot n} \quad (5)$$

Here $M_{fin,1}$ and $M_{fin,2}$ are the first and the second images of $M_{fin}$, respectively. $R_{mpfsl}$ is insensitive to the tissue parameters of the water pool. Under the condition that $R_{mpfsl}$ is much more sensitive to macromolecule proton fraction (MPF) than the other tissue parameters related to magnetization transfer or under the assumption that the other tissue parameter is nearly a constant, MPF may be calculated from $R_{mpfsl}$ using Bloch-McConnell equation, or by machine learning or deep learning methods. $R_{mpfsl}$ may be obtained under different values of $\Delta\omega$, $\omega_1$, and/or $$\frac{\Delta\omega}{\omega_1},$$

and may be used to calculate one or more tissue parameters related to magnetization transfer.

Furthermore, the magnetizations obtained by spin-lock RF trains may be inputted into machine learning or deep learning algorithms to obtain tissue parameters directly. These tissue parameters may carry important information for tissue characterization.

FIG. 1 is a flow chart illustrating a method for quantitative magnetic resonance imaging using spin-lock radio frequency trains in accordance with some examples of the present disclosure.

Figure 2:
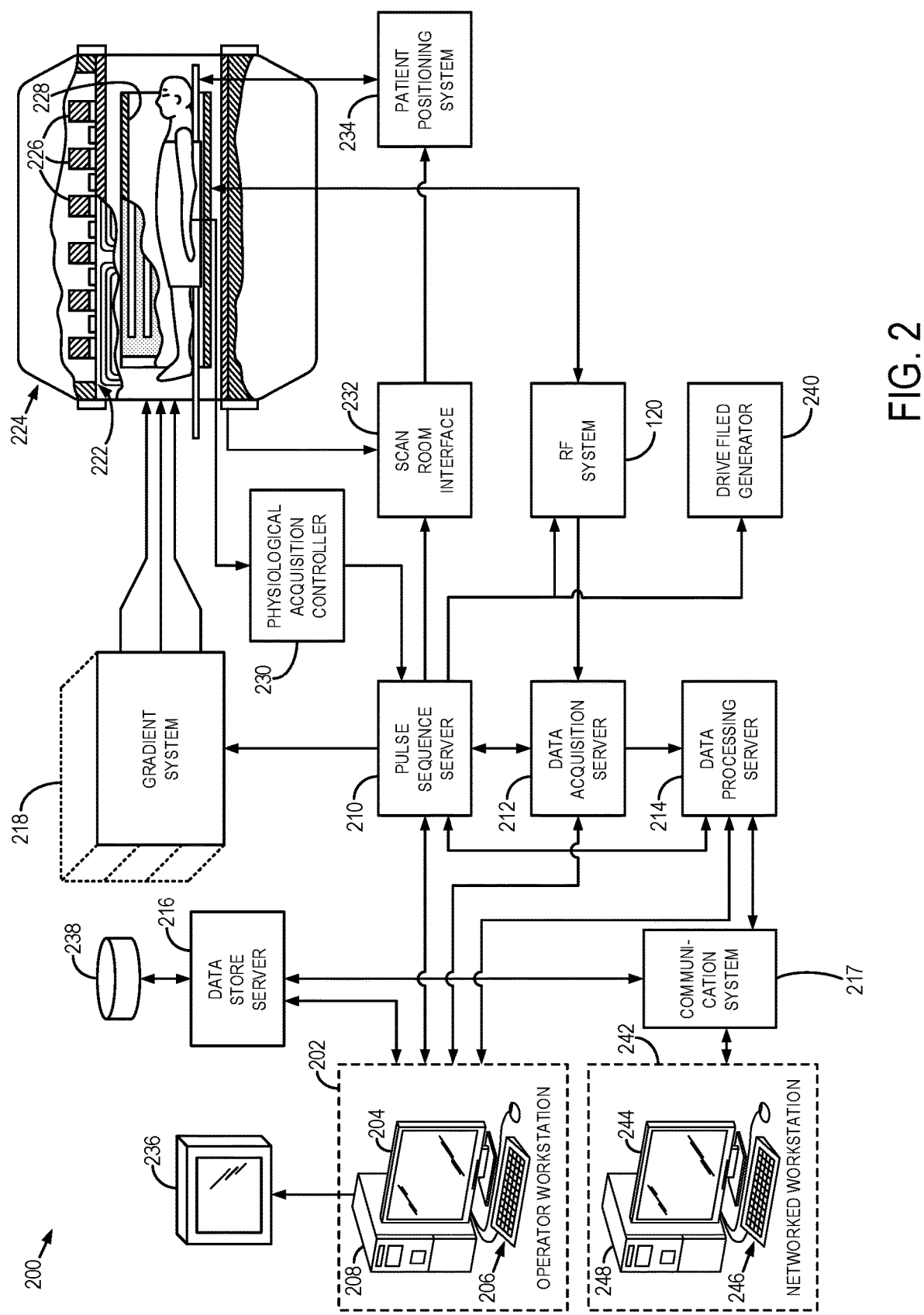
FIG. 2 illustrates an MRI system in accordance with some examples of the present disclosure.

At step 101, a target subject is arranged within an MRI system or apparatus. For example, as shown in FIG. 2 discussed below, a patient is arranged within the MRI system 200.

At step 102, a first MR image is obtained. For example, step 102 may include multiple steps 102-1, 102-2, and 102-3. At step 102-1, preparation 1 including zero, one or more preparatory sequences is applied. In 102-1, first a magnetization reset module is applied. This module is used to reset the magnetization to zero or a non-zero value under controlled condition. Suppression of blood signal, fluid signal, or fat signal may also be included in step 102-1.

At step 102-2, a first spin-lock RF train is applied. In step 102-2, a module of fat suppression may also be included and applied after the spin-lock RF train.

At step 102-3, a first magnetization signal is obtained.

After step 102, a second MR image is obtained at step 103.

At step 103, a second magnetization corresponding the second MR image is obtained based on a second initial magnetization different than the first initial magnetization that is used in obtaining the first magnetization and a same steady state magnetization as used in obtaining the first magnetization. In some examples, an initial magnetization may be modified by, but not limited to, at least one of following steps: using different time durations of relaxation before a spin-lock RF train, changing a phase, frequency modulation, a duration, or an amplitude of the head RF pulse in a first spin-lock module of the spin-lock RF train; changing the orientation of the effective spin-lock field; or applying one or more RF pulses with an arbitrary flip angle, a phase, frequency modulation, a duration, or an amplitude in front of the spin-lock RF train.

For example, step 103 may include multiple steps 103-1, 103-2, and 103-3. At step 103-1, preparation 2 including zero, one or more preparatory sequences is applied. At 103-1, first a magnetization reset module is applied. This module is used to reset the magnetization to zero or a non-zero value under controlled condition. Suppression of blood signal, fluid signal, or fat signal can also be included int 103-1.

At step 103-2, a second spin-lock RF train module is applied. In step 103-2, a module of fat suppression can also be included and applied after the spin-lock module. In step 103-3, a second magnetization signal is obtained. As discussed above, the second magnetization is obtained with an initial magnetization different than in obtaining the first image but the same steady state magnetization as in obtaining the first image.

In some examples, step 102 and step 103 are interchangeable. For example, the order to perform steps 102 and 103 can be changed and step 102 may be performed before or after step 103.

At step 104, a final magnetization is obtained based on the first magnetization obtained at step 102 and the second magnetization obtained at step 103.

In some examples, step 102, step 103, and step 104 may be repeatedly performed after a final magnetization is obtained at step 104 using different acquisition parameters including but not limited to TSL, Td, amplitude of spin-lock, and resonance frequency offset of spin-lock. A desired number of final magnetizations Mfin may be obtained after repeatedly performing steps 102, 103, and 104. Further, quantification may be performed based on the desired number of final magnetizations $M_{fin}$ obtained. In some examples, one final magnetizations $M_{fin}$ may be calculated based on one $M_{sl\_train\_1}$ and one $M_{sl\_train\_2}$ as obtained above. Two or more final magnetizations $M_{fin}$ may be obtained at different acquisition parameters used in 102 and 103. The desired number of final magnetizations $M_{fin}$ and quantification methods are flexible.

According to the examples of the present disclosure, a spin relaxation rate, $$R_{1\rho}\left(=\frac{1}{T_{1\rho}}\right),$$

may be calculated from an exponential relaxation model when using a train of spin-lock modules by fixing Td as a constant. It is also possible to calculate $R_{1\rho}$ and R1 simultaneously by varying TSL and Td, where R1 indicates a longitudinal relaxation rate. The present disclosure is applicable for quantification of single $R_{1\rho}$ in a mono-exponential relaxation model, two $R_{1\rho}$ in bi-exponential relaxation model, or more than two $R_{1\rho}$ in multiexponential relaxation model.

The $R_{1\rho}$ values may also be calculated directly by machine learning or deep learning using the first magnetization from 102, the second magnetization from 103, and their repetitions acquired at different acquisition parameters without calculating $M_{fin}$.

In some examples, step 102 and 103 may be repeated to obtain magnetizations at different resonance frequency offset (Δω) and spin-lock RF amplitude (ω₁) used in the spin-lock RF trains. Magnetization obtained at step 102 and 103 can be used to calculate $M_{fin}$ according to tissue parameters related to magnetization transfer. Moreover, one or more $R_{mpfsl}$ may be used to obtain one or more tissue parameters related to magnetization transfer.

In some examples, various magnetizations obtained at step 102 and 103 at different resonance frequency offset (Δω) and spin-lock RF amplitude (@₁) used in the spin-lock RF trains may be directly fed into machine learning and deep learning algorithm, and output one or more tissue parameters related to magnetization transfer.

In some examples, sensitivity of signals to tissue parameters related to magnetization transfer may be adjusted by adjusting the pulse sequence parameters of the first and second trains of spin-lock modules.

The method for the quantification using spin-lock RF train in accordance with the examples above of the present disclosure may be performed using an MRI system 200 as illustrated in FIG. 2. The MRI system 200 includes an operator workstation 202, which will typically include a display 204, one or more input devices 206, such as a keyboard and mouse, and a processor 208. The processor 208 may include a commercially available programmable machine running a commercially available operating system. The operator workstation 202 provides the operator interface that enables scan prescriptions to be entered into the MRI system 200. In general, the operator workstation 202 may be coupled to four servers: a pulse sequence server 110; a data acquisition server 212; a data processing server 214; and a data store server 216. The operator workstation 202 and each server 210, 212, 214, and 216 are connected to communicate with each other. For example, the servers 210, 212, 214, and 216 may be connected via a communication system 217, which may include any suitable network connection, whether wired, wireless, or a combination of both. As an example, the communication system 217 may include both proprietary or dedicated networks, as well as open networks, such as the internet.

The pulse sequence server 210 functions in response to instructions downloaded from the operator workstation 202 to operate a gradient system 218 and a RF system 120. Gradient waveforms necessary to perform the prescribed scan are produced and applied to the gradient system 218, which excites gradient coils in an assembly 122 to produce the magnetic field gradients, and used for position encoding magnetic resonance signals. The gradient coil assembly 122 forms part of a magnet assembly 224 that includes a polarizing magnet 226 and a whole-body RF coil 228.

RF waveforms are applied by the RF system 220 to the RF coil 228, or a separate local coil (not shown in FIG. 2), in order to perform the prescribed magnetic resonance pulse sequence. Responsive magnetic resonance signals detected by the RF coil 228, or a separate local coil (not shown in FIG. 2), are received by the RF system 220, where they are amplified, demodulated, filtered, and digitized under direction of commands produced by the pulse sequence server 210. The RF system 220 includes an RF transmitter for producing a wide variety of RF pulses used in MRI pulse sequences. The RF transmitter is responsive to the scan prescription and direction from the pulse sequence server 210 to produce RF pulses of the desired frequency, phase, and pulse amplitude waveform. The generated RF pulses may be applied to the whole-body RF coil 228 or to one or more local coils or coil arrays (not shown in FIG. 2). A drive field generator 240 is used to generate the desired electromagnetic drive field. For example, the drive field generator may include an external Solenoid, or a shielded solenoid, that is driven by a large amplifier at a low frequency. In some examples, an additional gradient amplifier can be utilized to drive the drive field generator.

The RF system 220 also includes one or more RF receiver channels. Each RF receiver channel includes an RF preamplifier that amplifies the magnetic resonance signal received by the coil 228 to which it is connected, and a detector that detects and digitizes the I and Q quadrature components of the received magnetic resonance signal. The magnitude of the received magnetic resonance signal may, therefore, be determined at any sampled point by the square root of the sum of the squares of the/and Q components:

$$M = \sqrt{I^2 + Q^2} \quad (6)$$

and the phase of the received magnetic resonance signal may also be determined according to the following relationship:

$$\varphi = \tan^{-1}\left(\frac{Q}{I}\right) \quad (7)$$

The pulse sequence server 210 also alternatively receives patient data from a physiological acquisition controller 230. In some examples, the physiological acquisition controller 230 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 132 that receives signals from various sensors associated with the condition of the patient and the magnet system. It is also through the scan room interface circuit 232 that a patient positioning system 234 receives commands to move the patient to desired positions during the scan.

The digitized magnetic resonance signal samples produced by the RF system 220 are received by the data acquisition server 212. The data acquisition server 212 operates in response to instructions downloaded from the operator workstation 202 to receive the real-time magnetic resonance data and provide buffer storage, such that no data is lost by data overrun. In some scans, the data acquisition server 212 does little more than passing the acquired magnetic resonance data to the data processor server 214. However, in scans that require information derived from acquired magnetic resonance data to control the further performance of the scan, the data acquisition server 212 is programmed to produce such information and convey it to the pulse sequence server 210. For example, during prescans, magnetic resonance data is acquired and used to calibrate the pulse sequence performed by the pulse sequence server 210. As another example, navigator signals may be acquired and used to adjust the operating parameters of the RF system 220 or the gradient system 218, or to control the view order in which k-space is sampled. In still another example, the data acquisition server 212 may also be employed to process magnetic resonance signals used to detect the arrival of a contrast agent in a magnetic resonance angiography (MRA) scan. In all these examples, the data acquisition server 212 acquires magnetic resonance data and processes it in real-time to produce information that is used to control the scan.

The data processing server 214 receives magnetic resonance data from the data acquisition server 212 and processes it in accordance with instructions downloaded from the operator workstation 202. Such processing may, for example, include one or more of the following: reconstructing two-dimensional or three-dimensional images by performing a Fourier transformation of raw k-space data; performing other image reconstruction algorithms, such as iterative or back projection reconstruction algorithms; applying filters to raw k-space data or to reconstructed images; generating functional magnetic resonance images; calculating motion or flow images; and so on.

Images reconstructed by the data processing server 214 are conveyed back to the operator workstation 202 where they are stored. Real-time images are stored in a data base memory cache (not shown in FIG. 2), from which they may be output to operator display 212 or a display 136 that is located near the magnet assembly 224 for use by attending physicians. Batch mode images or selected real time images are stored in a host database on disc storage 138. When such images have been reconstructed and transferred to storage, the data processing server 214 notifies the data store server 216 on the operator workstation 202. The operator workstation 202 may be used by an operator to archive the images, produce films, or send the images via a network to other facilities.

The MRI system 200 may also include one or more networked workstations 142. By way of example, a networked workstation 242 may include a display 244; one or more input devices 246, such as a keyboard and mouse; and a processor 248. The networked workstation 242 may be located within the same facility as the operator workstation 202, or in a different facility, such as a different healthcare institution or clinic.

The networked workstation 242, whether within the same facility or in a different facility as the operator workstation 202, may gain remote access to the data processing server 214 or data store server 216 via the communication system 217. Accordingly, multiple networked workstations 242 may have access to the data processing server 214 and the data store server 216. In this manner, magnetic resonance data, reconstructed images, or other data may exchange between the data processing server 214 or the data store server 216 and the networked workstations 142, such that the data or images may be remotely processed by a networked workstation 242. This data may be exchanged in any suitable format, such as in accordance with the transmission control protocol (TCP), the internet protocol (IP), or other known or suitable protocols.

In some examples, there is also provided an apparatus for quantitative MRI, such as the MRI system 200. The apparatus may include one or more processors and a memory configured to store instructions executable by the one or more processors. Further, the one or more processors, upon execution of the instructions, are configured to perform acts including: obtaining a first magnetization signal based on a first spin-lock train, obtaining a second magnetization based on a second spin-lock train, and obtaining a final magnetization signal based on the first magnetization signal and the second magnetization signal.

In some examples, each of the first spin-lock train and the second spin-lock train include a trains of spin lock RF clusters with each spin-lock RF pulse cluster followed by an idle time without RF irradiation with a duration of Td, where the spin lock RF cluster may include a spin lock RF pulse with a duration of time-of-spin-lock (TSL), a head RF pulse, and a tail RF pulse, where the spin lock RF pulse is sandwiched between the head and the tail RF pulses. For example, the first spin-lock train and the second spin-lock train may be respectively illustrated in FIG. 3.

In some examples, the duration of TSL, the duration of Td, the orientation of spin-lock field may be different in each spin-lock module.

In some examples, one or more processors may further repeat steps of obtaining the first magnetization signal and the second magnetization signal to obtain one or more final magnetization signals. As shown in FIG. 1, step 102, step 103, and step 104 may repeated at the desired numbers to obtain multiple final magnetization signals.

In some examples, one or more processors may further perform quantification based on all final magnetization signals obtained after repeating the steps of obtaining the first magnetization signal and the second magnetization signal.

In some examples, one or more processors may further obtain one or more final magnetization signals at different resonance frequency offset and spin-lock RF amplitude used in the train of spin-lock modules. The magnetization signals can be used to calculate tissue parameters related to magnetization transfer based on Bloch-McConnell equations. In some examples, one or more processors may further feed the all final magnetization signals into an artificial intelligence system, e.g., machine learning or deep learning system, and outputting one or more tissue parameters related to magnetization transfer.

The above methods may be implemented using an apparatus that includes one or more circuitries, which include application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components. The apparatus may use the circuitries in combination with the other hardware or software components for performing the above described methods. Each module, sub-module, unit, or sub-unit disclosed above may be implemented at least partially using the one or more circuitries.

Other examples of the disclosure will be apparent to those skilled in the art from consideration of the specification and practice of the disclosure disclosed here. This application is intended to cover any variations, uses, or adaptations of the disclosure following the general principles thereof and including such departures from the present disclosure as come within known or customary practice in the art. It is intended that the specification and examples be considered as exemplary only.

It will be appreciated that the present disclosure is not limited to the exact examples described above and illustrated in the accompanying drawings, and that various modifications and changes can be made without departing from the scope thereof.

What is claimed is:

1. A method for quantitative magnetic resonance imaging (MRI), comprising:
    obtaining a first magnetization signal based on a first train of spin-lock modules, wherein the first train of spin-lock modules is performed on a first initial magnetization;
    obtaining a second magnetization signal based on a second train of spin-lock modules, wherein the second train of spin-lock modules is performed on a second initial magnetization different from the first initial magnetization; and
    obtaining a final magnetization signal based on the first magnetization signal and the second magnetization signal.

2. The method of claim 1, wherein at least one spin-lock module in the first train of spin-lock modules and the second train of spin-lock modules comprises a spin lock radiofrequency (RF) cluster and an idle time without RF irradiation with a duration of Td following the spin lock RF cluster.

3. The method of claim 2, wherein the spin lock RF cluster comprises a head RF pulse, a tail RF pulse, and a spin lock RF pulse with a duration of time-of-spin-lock (TSL), an amplitude of spin lock RF pulse, and a resonance frequency offset, and the spin lock RF pulse is sandwiched between the head and the tail RF pulses, and a crusher gradient follows the tail RF pulse.

4. The method of claim 1, further comprising:
    modifying an initial magnetization by at least one of following steps:
    using different time durations of relaxation before a spin-lock RF train;
    changing a phase, frequency modulation, a duration, or an amplitude of the head RF pulse in a first spin-lock module of the spin-lock RF train; or
    applying one or more RF pulses with an arbitrary flip angle, a phase, frequency modulation, a duration, or an amplitude in front of the spin-lock RF train.

5. The method of claim 3, wherein pulse sequence parameters in each spin-lock module in the first train of spin-lock modules and the second train of spin-lock modules are same or different, wherein the pulse sequence parameters comprise at least one of following parameters: the duration of TSL, the amplitude of spin-lock RF pulse, the resonance frequency offset of the spin-lock RF pulse, the duration of Td, area of crusher gradient, or orientation of spin-lock field.

6. The method of claim 3, further comprising:
    obtaining one or more final magnetization signals by repeating steps of obtaining the first magnetization signal and the second magnetization signal, wherein a duration of TSL or a duration of Td in repeating is different from the duration of TSL or the duration of Td used in obtaining the first magnetization signal or the second magnetization signal.

7. The method of claim 6, further comprising:
performing qualification based on all final magnetization signals obtained after repeating the steps of obtaining the first magnetization signal and the second magnetization signal.

8. The method of claim 3, further comprising:
obtaining all final magnetization signals at different resonance frequency offset and amplitude of spin lock RF pulse in the first and second train of spin-lock modules, wherein the all final magnetization signals comprise the final magnetization signal obtained based on the first magnetization signal and the second magnetization signal and the one or more final magnetization signals obtained in repeating the steps of obtaining the first magnetization signal and the second magnetization signal.

9. The method of claim 8, further comprising:
feeding the all final magnetization signals into a machine learning or artificial intelligence system and outputting one or more tissue parameters, or
using Bloch-McConnell equations to calculate one or more tissue parameters from the all final magnetization signals.

10. The method of claim 8, further comprising:
adjusting sensitivity of signals to tissue parameters related to magnetization transfer by adjusting the pulse sequence parameters of the first and second trains of spin-lock modules.

11. The method of claim 1, wherein the first train of spin-lock modules is performed after a first duration of relaxation, and the second train of spin-lock modules is performed after a second duration of relaxation different from the first duration of relaxation.

12. An apparatus for quantitative magnetic resonance imaging (MRI), comprising: one or more processors; and
a memory configured to store instructions executable by the one or more processors; wherein the one or more processors, upon execution of the instructions, are configured to perform a method for quantitative MRI, comprising:
obtaining a first magnetization signal based on a first train of spin-lock modules, wherein the first train of spin-lock modules is performed on a first initial magnetization;
obtaining a second magnetization signal based on a second train of spin-lock modules, wherein the second train of spin-lock modules is performed on a second initial magnetization different from the first initial magnetization; and
obtaining a final magnetization signal based on the first magnetization signal and the second magnetization signal.

13. The apparatus of claim 12, wherein at least one spin-lock module in the first train of spin-lock modules and the second train of spin-lock modules comprises a spin lock radiofrequency (RF) cluster and an idle time without RF irradiation with a duration of Td following the spin lock RF cluster.

14. The apparatus of claim 13, wherein the spin lock RF cluster comprises a head RF pulse, a tail RF pulse, and a spin lock RF pulse with a duration of time-of-spin-lock (TSL), an amplitude of spin lock RF pulse, and a resonance frequency offset, and the spin lock RF pulse is sandwiched between the head and the tail RF pulses, and a crusher gradient follows the tail RF pulse.

15. The apparatus of claim 12, wherein the method further comprises:
modifying an initial magnetization by at least one of following steps:
using different time durations of relaxation before a spin-lock RF train;
changing a phase, frequency modulation, a duration, or an amplitude of the head RF pulse in a first spin-lock module of the spin-lock RF train; or
applying one or more RF pulses with an arbitrary flip angle, a phase, frequency modulation, a duration, or an amplitude in front of the spin-lock RF train.

16. The apparatus of claim 14, wherein pulse sequence parameters in each spin-lock module in the first train of spin-lock modules and the second train of spin-lock modules are same or different, wherein the pulse sequence parameters comprise at least one of following parameters: the duration of TSL, the amplitude of spin-lock RF pulse, the resonance frequency offset of the spin-lock RF pulse, the duration of Td, area of crusher gradient, or orientation of spin-lock field.

17. The apparatus of claim 14, wherein the method further comprises:
obtaining one or more final magnetization signals by repeating steps of obtaining the first magnetization signal and the second magnetization signal, wherein a duration of TSL or a duration of Td in repeating is different from the duration of TSL or the duration of Td used in obtaining the first magnetization signal or the second magnetization signal.

18. The apparatus of claim 17, wherein the method further comprises:
performing qualification based on all final magnetization signals obtained after repeating the steps of obtaining the first magnetization signal and the second magnetization signal.

19. The apparatus of claim 12, wherein the first train of spin-lock modules is performed after a first duration of relaxation, and the second train of spin-lock modules is performed after a second duration of relaxation different from the first duration of relaxation.

20. A non-transitory computer-readable storage medium for storing computer-executable instructions that, when executed by one or more computer processors, cause the one or more computer processors to perform a method for quantitative MRI, comprising:
obtaining a first magnetization signal based on a first train of spin-lock modules, wherein the first train of spin-lock modules is performed on a first initial magnetization;
obtaining a second magnetization signal based on a second train of spin-lock modules, wherein the second train of spin-lock modules is performed on a second initial magnetization different from the first initial magnetization; and
obtaining a final magnetization signal based on the first magnetization signal and the second magnetization signal.

* * * * *